United States Patent
Li et al.

(10) Patent No.: US 10,974,225 B1
(45) Date of Patent: Apr. 13, 2021

(54) METAL OXIDE COATED CERAMIC CORRUGATED PLATE CATALYST, PREPARATION AND APPLICATION IN PREPARATION OF KEY INTERMEDIATES OF CITRAL

(71) Applicants: ZHEJIANG NHU COMPANY LTD., Zhejiang (CN); ZHEJIANG UNIVERSITY, Zhejiang (CN); SHANDONG NHU PHARMACEUTICAL CO., LTD., Shandong (CN)

(72) Inventors: Haoran Li, Zhejiang (CN); Xiao Ma, Shandong (CN); Yong Wang, Zhejiang (CN); Baishan Hu, Zhejiang (CN); Dan Qiu, Zhejiang (CN); Jianyong Mao, Shandong (CN); Bing Lu, Zhejiang (CN); Shanjun Mao, Zhejiang (CN); Lili Yu, Zhejiang (CN); Qichuan Li, Zhejiang (CN)

(73) Assignees: ZHEJIANG NHU COMPANY LTD., Zhejiang (CN); ZHEJIANG UNIVERSITY, Zhejiang (CN); SHANDONG NHU PHARMACEUTICAL CO., LTD., Shandong (CN)

( * ) Notice: Subject to any disclaimer, the term of this patent is extended or adjusted under 35 U.S.C. 154(b) by 0 days.

(21) Appl. No.: 16/919,092

(22) Filed: Jul. 1, 2020

Related U.S. Application Data

(63) Continuation of application No. PCT/CN2020/081042, filed on Mar. 25, 2020.

(30) Foreign Application Priority Data

Jan. 17, 2020 (CN) .......................... 202010054866.6

(51) Int. Cl.
*B01J 23/00* (2006.01)
*B01J 23/889* (2006.01)
(Continued)

(52) U.S. Cl.
CPC ............. *B01J 23/002* (2013.01); *B01J 21/06* (2013.01); *B01J 23/881* (2013.01);
(Continued)

(58) Field of Classification Search
CPC ......... C07C 29/56; B01J 23/002; B01J 23/85; B01J 23/847; B01J 23/881; B01J 23/889;
(Continued)

(56) References Cited

U.S. PATENT DOCUMENTS 3,655,735 A * 4/1972 Pommer ............... C07C 69/145
560/261
3,925,485 A 12/1975 Chabardes et al.
(Continued)

FOREIGN PATENT DOCUMENTS

CN 101381292 2/2012
CN 101381283 3/2012
(Continued)

OTHER PUBLICATIONS

JP S53138992, Nishimoto, K., et al., Catalyst useful in redn. of nitrogen oxide of oxidn. of sulphur oside, mfd. by fixing oxide of tungsten, vanadium, titanium etc. on cermac support, 5 pages, English translation (Year: 1978).*
(Continued)

*Primary Examiner* — Yate' K Cutliff
(74) *Attorney, Agent, or Firm* — JCIP Global Inc.

(57) ABSTRACT

The present disclosure belongs to the technical field of catalysis, and particularly relates to a metal oxide coated ceramic corrugated plate catalyst, its preparation method and application thereof in preparation of key intermediates
(Continued)

of citral. The catalyst consists of a ceramic corrugated plate carrier and a metal oxide active layer coated on a surface of the carrier, wherein the metal oxide active layer is a metal oxide formed by active ingredient titanium and at least four other metal elements selected from vanadium, chromium, manganese, iron, zirconium, niobium and molybdenum.

15 Claims, 2 Drawing Sheets

(51) Int. Cl.
    *C07C 29/56* (2006.01)
    *B01J 23/881* (2006.01)
    *B01J 37/02* (2006.01)
    *B01J 37/08* (2006.01)
    *B01J 35/04* (2006.01)
    *B01J 21/06* (2006.01)

(52) U.S. Cl.
    CPC ........... *B01J 23/8898* (2013.01); *B01J 35/04* (2013.01); *B01J 37/0219* (2013.01); *B01J 37/088* (2013.01); *C07C 29/56* (2013.01)

(58) Field of Classification Search
    CPC ...... B01J 23/8898; B01J 35/04; B01J 37/219; B01J 21/06
    See application file for complete search history.

(56) References Cited

U.S. PATENT DOCUMENTS

| | | | | |
|---|---|---|---|---|
| 4,028,424 | A | | 6/1977 | Yoshida et al. |
| 4,219,683 | A | | 8/1980 | Wu |
| 4,749,814 | A | * | 6/1988 | Chabardes ............ C07C 45/512 568/310 |
| 6,013,843 | A | * | 1/2000 | Aquila .................. B01J 8/0242 568/450 |
| 8,551,901 | B2 | * | 10/2013 | Shinoda ................ F01N 3/2066 502/73 |
| 2005/0143597 | A1 | | 6/2005 | Mizushima et al. |
| 2012/0328499 | A1 | * | 12/2012 | Ando .................... F01N 13/0093 423/213.5 |
| 2017/0173567 | A1 | * | 6/2017 | Bai ....................... B01J 35/1014 |
| 2019/0077736 | A1 | * | 3/2019 | Dehn ..................... B01J 23/52 |
| 2019/0217279 | A1 | * | 7/2019 | Lim ........................ B01J 37/08 |

FOREIGN PATENT DOCUMENTS

| | | | | |
|---|---|---|---|---|
| CN | 102701910 | * | 10/2012 | ............ C07C 29/56 |
| CN | 104148055 | * | 11/2014 | ............ B01D 53/56 |
| CN | 105503553 | | 4/2016 | |
| CN | 105967978 | | 9/2016 | |
| CN | 109046377 | * | 12/2018 | ............ B01J 23/889 |
| CN | 109336750 | | 2/2019 | |
| CN | 110560115 A | * | 12/2019 | ............ B01J 27/24 |
| JP | S5745121 | | 3/1982 | |
| JP | S53138992 A | * | 4/1984 | ............ B01D 53/94 |
| JP | H04027440 | * | 1/1992 | ............ B01J 19/32 |
| WO | 2008037693 | | 4/2008 | |
| WO | 2016059155 | | 4/2016 | |

OTHER PUBLICATIONS

CN 110560115, Chen, L. et al., Catalyst for synthesizing trimellitic anhydride, 7 pages, English translation (Year: 2019).*
CN 102701910, Zhang, S., et al., Method for preparing prenol by isomerization 3-methyl-3-butene-1-ethanol, 4 pages, English translation (Year: 2012).*
CN 109046377, Wang, L. et al., Heterogeneous catalyst for hydrogenperoxide catalysis as well as preparation method andapplication thereof, 9 pages, English translation (Year: 2018).*
JP H0427440, Honchi, A. et al., Planar catalyst and manufacture thereof, 9 pages, English translation (Year: 1992).*
CN 104148055(A), Honghua, S., Denitration catalyst, English translation 7 pages (Year: 2014).*

* cited by examiner

METAL OXIDE COATED CERAMIC CORRUGATED PLATE CATALYST, PREPARATION AND APPLICATION IN PREPARATION OF KEY INTERMEDIATES OF CITRAL

CROSS-REFERENCE TO RELATED APPLICATION

This application is a continuation of international PCT application Serial no. PCT/CN2020/081042, filed on Mar. 25, 2020, which claims the priority benefit of China applications no. 202010054866.6, filed on Jan. 17, 2020. The entirety of each of the above-mentioned patent applications is hereby incorporated by reference herein and made a part of this specification.

BACKGROUND

Technical Field

The present disclosure belongs to the technical field of catalysis, and particularly relates to a metal oxide coated ceramic corrugated plate catalyst, its preparation and application thereof in preparation of key intermediates of citral.

Description of Related Art

Citral is a terpenoid fatty aldehyde with a strong lemon aroma. Citral is an important spice intermediate, which can be used to produce citrus flavor food spices, or to synthesize other spices such as isopulegol, hydroxycitronellal and ionone. More importantly, citral is an important starting material for the synthesis of isophytol, vitamin E and vitamin A.

Citral exists naturally in litsea cubeba oil and can be obtained by vacuum distillation extraction. However, due to the limitation of raw material sources and production process efficiency, it does not meet the requirements of large-scale production of modern engineering and cannot meet the market demand. Therefore, the majority of citral on the market is chemically synthesized by the following methods: condensation and rearrangement of alcohols and aldehydes, dehydrolinalool direct rearrangement method, geraniol gas phase oxidation method, isoprene method and nitrogen oxide method.

The method of condensation and rearrangement of alcohols and aldehydes: according to the method, prenol and prenal are condensed to generate 3-methyl-2-butene-1-aldehyde diisopentenyl acetal, and then 3-methyl-2-butene-1-aldehyde diisopentenyl acetal is cracked and rearranged to obtain citral. This method is environment-friendly with high atomic utilization ratio and is most competitive in industry.

The industrial method for preparing the key intermediates of citral, prenol and prenal, is mainly the isobutene method:

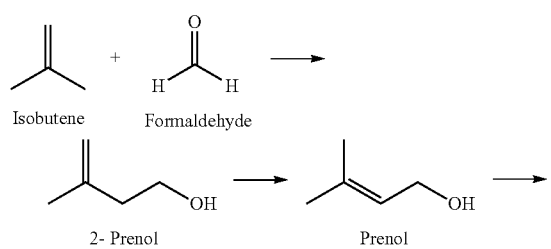

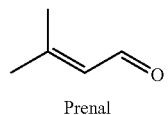

Prenal

U.S. Pat. No. 4,028,424, WO 2008037693, U.S. Pat. No. 4,219,683, etc. disclose processes of the route. However, the raw material isobutene of the route is prone to polymerize when heated, and it is almost industrially obtained from refinery gas and cracked C4 fraction, and the source of raw material is limited.

The two key intermediates, namely prenol and prenal, involved in the method can be obtained through a multi-step reaction by taking acetone as a raw material:

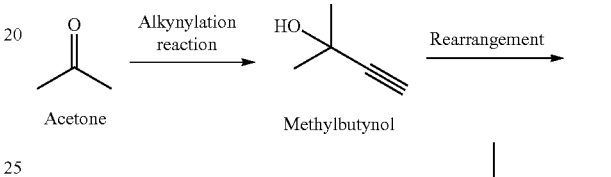

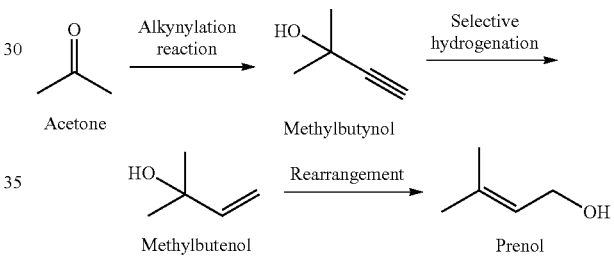

At present, the route for preparing citral has not yet been industrialized. This route uses acetone as raw material to produce prenol and prenal, and then performs condensation and rearrangement to prepare citral. The reason lies in that the preparation of prenol or prenal by isomerization rearrangement reaction has problems including low conversion rate, difficult to control side reaction, much by-products, high catalyst price, difficult to recycle and apply, large dosage needed and the like:

U.S. Pat. No. 3,925,485 uses methylbutenol as raw material and reacts under the catalysis of linalyl vanadate to prepare prenol with a conversion rate of 25.6% and a selectivity of 83%. Patent JP 57045121 uses silanol vanadate as a catalyst. The conversion rate of 3-methyl-3-butenol is 30%, and the recovery rate of raw materials and products is less than 50%. Patent CN 105967978A discloses using vanadium oxides or metal salts comprising vanadium as catalysts with the conversion of less than 30%.

Patent CN 101381283B uses methylbutenol as raw material to continuously prepare prenol with rhenium and tungsten as catalysts and rectification conditions. However, the selectivity of the product to prenol is up to 46%, the crude product obtained by the reaction needs secondary rectification separation, and the reaction energy consumption is high.

Patent US 2005/143597 uses methylbutynol as raw material, methyl (triphenylphosphine) gold and sulfuric acid as catalyst to prepare prenal. The yield is only 44%, and the catalyst which is methyl (triphenylphosphine) gold needs to be dissolved in methanol, the sulfuric acid uses an aqueous solution, and the reaction system is complex with using the solvent in the reaction process.

Patent CN 105503553 mentions the preparation of α,β-unsaturated carbonyl compounds from substituted propargyl alcohol by Meyer-Schuster rearrangement with cation-modified montmorillonite as catalyst and substituted propargyl alcohol as raw materials. With metal-modified montmorillonite as catalyst, the reaction time is up to 36 hours, and the patent uses nitromethane as solvent, which is more dangerous.

Patent WO 2016059155A1 mentions a similar reaction in which an unsaturated ketone is prepared by rearrangement of a substituted alkynol, with titanium oxide acetylacetonate and cuprous chloride as catalysts, the target compound is prepared with toluene as a solvent for 18 hours, and the reaction time is long.

Patent CN 109336750A discloses a process for the synthesis of prenal. Prenal is prepared by catalytic rearrangement of 2-methyl-3-butyne-2-ol with a metal oxide as a catalyst in the presence of an auxiliary agent. During the synthesis reaction, the content of 2-methyl-3-butyne-2-ol decreases from 99.7% to 56% then keeps unchanged, that is, the conversion rate is unchanged, the reaction is balanced, and the end point is reached. So the conversion rate per pass of the raw material of 2-methyl-3-butyne-2-ol is only 43.8%; the yield per pass of prenal is lower.

CN 101381292B discloses a method for continuously producing prenal. A composite catalyst composed of titanium oxide acetylacetonate, cuprous chloride and benzoic acid is adopted to realize continuous production of methylbutynol to prenal via a reactive distillation coupling technology with the overall yield reaching 88-93%. However, the catalyst is high in price and difficult to recycle and apply, the raw materials remain in a tower kettle for a long time, and the dehydroxylation byproducts of the raw materials are not easy to control, all resulting in more by-products in practical applications.

SUMMARY

In order to solve the above problems existing in the prior art, one of the objects of the present disclosure is to provide a metal oxide coated ceramic corrugated plate catalyst.

Another object of the present disclosure is to provide a method for preparing the metal oxide coated ceramic corrugated plate catalyst.

Still another object of the present disclosure is to provide a method for continuously preparing prenal or prenol with the catalyst.

In order to achieve the objects of the present disclosure above, one of the technical scheme of the present disclosure is as follows:

A metal oxide coated ceramic corrugated plate catalyst, consisting of a ceramic corrugated plate carrier and a metal oxide active layer coated on a surface of the carrier, wherein the metal oxide active layer is a metal oxide formed by active ingredient titanium and at least four other metal elements selected from vanadium, chromium, manganese, iron, zirconium, niobium and molybdenum.

Preferably, the metallic element comprises vanadium and/or molybdenum.

Preferably, the metal oxide active layer has a thickness of 0.1-100 μm.

Preferably, the ceramic corrugated plate has a thickness of 0.5-1 mm.

Preferably, the ceramic corrugated plate has a corrugation inclination angle of 30-45°.

Preferably, the ceramic corrugated plate has a peak height and a wave distance of 5-30 mm.

Preferably, the loading amount of the metal oxide active layer is 0.1-10 wt %, further preferably 0.5-10 wt %, 0.5-9 wt %, 0.5-8 wt %, 0.5-6.5 wt %, 0.5-6.2 wt %, 0.5-6 wt %, 0.5-5.5 wt %, 0.5-5 wt %, 1-5 wt %, 1.2-5 wt %, 1.5-5 wt %, 2-5 wt % of the ceramic corrugated plate.

Preferably, the ceramic corrugated plate is made of cordierite, alumina or silicon carbide.

As one of the embodiments, the metal oxide coated ceramic corrugated plate catalyst, wherein the metal oxide active layer is a metal oxide formed by Ti and four metal elements of V, Mn, Fe and Mo, wherein the molar ratio of all the metal elements in the metal oxide is 1-1.5:1-1.2:1:1:1. The above ratio is further preferably 1-1.2:1:1:1:1.

As another embodiment, the metal oxide coated ceramic corrugated plate catalyst, wherein the metal oxide active layer is a metal oxide formed by Ti and four metal elements of V, Zr, Cr and Mo, wherein the molar ratio of all the metal elements in the metal oxide is 1-1.5:1-1.2:1:1:1. The above ratio is further preferably 1-1.1:1.2:1:1:1.

As another embodiment, the metal oxide coated ceramic corrugated plate catalyst, wherein the metal oxide active layer is a metal oxide formed by Ti and four metal elements of V, Nb, Fe and Mo, wherein the molar ratio of all the metal elements in the metal oxide is 1-1.2:1-1.2:0.6-1:1:1. The above ratio is further preferably 1-1.1:1-1.2:0.8-1:1:1.

The present disclosure also provides a method for preparing the metal oxide coated ceramic corrugated plate catalyst, which includes the following steps:

(1) dissolving salts comprising at least four metal elements in titanium sol to form uniform mixed colloidal liquid;

(2) carrying out spray drying on the mixed colloidal liquid on the surface of the ceramic corrugated plate and high-temperature calcination to obtain the metal oxide coated ceramic corrugated plate catalyst.

Preferably, the metal element is selected from vanadium, chromium, manganese, iron, zirconium, niobium and molybdenum.

Further preferably, the metallic element comprises vanadium and/or molybdenum. Under the preparation method above, vanadium or molybdenum can form an oxide form of vanadate or molybdate, so that the metal oxide adhesion is more stable.

Preferably, in step (1), the titanium sol is titanium dioxide or butyl titanate sol.

Preferably, the titanium sol is controlled to have a pH of 1-5, further preferably 2-5, 2-4, 3-4.

Preferably, the titanium sol has a mass concentration of 10-30% and the solvent is water.

Preferably, the titanium sol further comprises a surfactant in an amount of 1-5 wt % of the titanium sol.

As a surfactant, an anionic surfactant, a cationic surfactant, a zwitterionic surfactant, a nonionic surfactant or a mixture of any of the foregoing can be used.

Examples of suitable anionic surfactants are ammonium alkyl sulfates such as ammonium lauryl sulfate and the like.

Examples of suitable cationic surfactants are cetrimonium bromide, cetylpyridinium chloride, benzalkonium chloride, benzethonium chloride and the like. Examples of suitable zwitterionic surfactants are (3-[(3-cholamidopropyl) dimethylammonio]-1-propanesulfonate) (CHAPS), cocamidopropyl hydroxysultaine, cocamidopropyl betaine, and the like.

Examples of suitable nonionic surfactants are polyethylene glycol alkyl ethers, glucoside alkyl ethers, polyethylene glycol octylphenyl ethers, polyethylene glycol alkylphenyl ethers, glycerol alkyl esters, polyoxyethylene glycol sorbitan alkyl esters, block copolymers (such as poloxamers) and polyethoxylated tallow amines and the like.

The salts can be, for example, nitrates, chlorides, sulfates, carbonates, citrates, 2-O-β-D-Glucopyranosyl-L-ascorbate, succinates, preferably nitrates, citrates. The salt further comprises ammonium molybdate and ammonium vanadate.

The amount of the salts used is based on the metal elements and the molar ratio between any two of the salts is 0.8-1.2:1. The molar ratio of the amount of the salt (single component) to the titanium sol is 0.8-1.2:1 (in terms of metal elements).

Preferably, in step (1), salts of 4 to 5 different metal elements are dissolved in the titanium sol.

Preferably, in step (2), the spray drying temperature is 80420° C., further preferably 90410° C., 100-120° C., 100-110° C., 100-105° C., 80410° C. and 90-110° C.

Preferably, the mixed colloidal liquid is used in an amount of 0.5-15 wt % of the ceramic corrugated plate, further preferably 1-15 wt %, 1-12 wt %, 1-10 wt %, 1-9 wt %, 1-8 wt %, 1-7 wt %, 1-6 wt %, 1-5 wt %.

Preferably, in step (2), the ceramic corrugated plate is cleaned before spray drying. The cleaning is water washing, acid washing or ultrasonic water washing, preferably ultrasonic water washing. The ultrasonic water washing can increase the roughness of the surface of the ceramic corrugated plate and improve the adhesion performance of the catalyst.

Preferably, in step (2), the high-temperature calcination temperature is 700-1400° C., further preferably 750-1400° C., 800-1400° C., 900-1400° C., 900-1300° C., 900-1200° C.

The high-temperature calcination time is 2-8 h, preferably 2-7 h, 2-6 h, 3-6 h, 3-5 h. The calcination atmosphere is an air atmosphere.

In the present disclosure, salts of different metal elements are directly dissolved in titanium sol and then sprayed onto the ceramic corrugated plate. After high-temperature calcination, a stable metal oxide coated ceramic corrugated plate catalyst is directly formed. The prepared catalyst of the present disclosure is stable in structure, and meanwhile the separation function of the ceramic corrugated plate is retained. Surprisingly, the catalyst has excellent catalytic activity performance in preparing the citral key intermediates prenal and prenol by isomerizing.

The present disclosure also provides a method for continuously preparing prenal or prenol by utilizing the catalyst, which comprises the following steps of:

Filling the reaction zone of the rectifying tower with the metal oxide coated ceramic corrugated plate catalyst described above, correspondingly continuously introducing methylbutynol or methylbutenol into the rectifying tower for catalytic rearrangement reaction, and continuously extracting prenal or prenol from the lateral line of the tower kettle.

Preferably, the temperature of the catalytic rearrangement reaction in the reaction zone is 80-150° C., further preferably 80-130° C., 90-130° C., 100-130° C., 110-130° C., 120-130° C.

Preferably, the pressure of the catalytic rearrangement reaction in the reaction zone is 0-0.2 MPa, further preferably 0.01-0.2 MPa, 0.01-0.15 MPa, 0.01-0.12 MPa, 0.01-0.1 MPa.

The feed temperature of methylbutynol according to the present disclosure is not particularly limited, and is preferably 20-100° C.

The water content of the methylbutynol is not particularly limited, but it is preferable that the water content of the methylbutynol is less than 5%, further less than 1%, for the reaction to proceed efficiently.

In order to realize continuous production, a reaction rectifying tower system with a specific structure is adopted in the present disclosure. The reaction rectifying tower system comprises two reaction zones and three separation zones from top to bottom, and the two separation zones are arranged between the three separation zones; and a feed inlet is arranged between the two reaction zones. Unreacted methylbutenol or methylbutynol is separated from prenol or prenal by distillation under reaction conditions and is extracted from the top of the rectifying tower. The extracted methylbutenol or methylbutynol is directly refluxed to the top of the rectifying tower after being condensed, and the other part is combined with the feed stream and recycled to the reaction zone of the rectifying tower for reaction.

Preferably, the reflux ratio of methylbutenol or methylbutynol withdrawn after condensation to the top of the rectifying tower to methylbutenol or methylbutynol recycled back to the reaction zone is controlled to be 5-8:1.

Preferably, the condensation temperature is 80-100° C.

Preferably, the rectifying tower is a packed tower, and the theoretical number of packed trays in the reaction zone of the packed tower is 3-15, further preferably 3-12, 3-10, 5-12, 5-10, respectively.

The three separation zones can be provided with separation trays, such as floating valves, sieve plates, bubble caps and the like; various bulk or regular packing can also be packed, such as Pall rings, θ rings, saddle-shaped packing, stepped ring packing, corrugated plate packings, corrugated gauze packing and the like; it may also be a ceramic corrugated plate coated with a metal oxide. Generally, the three separation zones have a theoretical tray number of 5-50.

Preferably, one of the three separation zones is located above the reaction zone and the other two are located below the reaction zone respectively, and from top to bottom are a first separation zone, a second separation zone and a third separation zone respectively. The first separation zone has a theoretical tray number of 5-20, the second separation zone has a theoretical tray number of 20-50, and the third separation zone has a theoretical tray number of 5-20.

Compared with the prior art, the present disclosure has the following beneficial effects:

(1) The present disclosure provides a catalyst suitable for continuously producing prenal or prenol. By using the catalyst for preparing prenal or prenol through catalytic rearrangement reaction, the purity and yield of the product are high, the raw material conversion rate is high, and the catalyst selectivity is good.

(2) The metal oxide coated ceramic corrugated plate catalyst provided by the present disclosure integrates the functions of catalysis and separation into a whole with high stability and can be directly used for continuous rectification reaction.

DESCRIPTION OF THE EMBODIMENTS

Example 1

Preparation of $(Ti_{1.1}V_1Mn_1Fe_1Mo_1)O_{11.2}$ Metal Oxide Coated Ceramic Corrugated Plate Catalyst (1) 1 mol ammonium vanadate, 1 mol ferric trichloride, 1 mol molybdenum citrate and 1 mol manganese chloride were added into 1.1 mol titanium dioxide sol (concentration 20%, pH 3), dissolved by ultrasonic waves, and completely and uniformly mixed to obtain mixed colloidal liquid.

(2) The mixed colloidal liquid were spray dried on a surface of ceramic corrugated plate with the weight of 5.5 Kg, thickness of 1 mm, corrugation inclination angle of 45° and wave crest height of 30 mm and wave distance of 10 mm under the condition of 110° C., then placed in a muffle furnace and calcined under air atmosphere with temperature increased to 950° C. at 5° C./min for 6 h. $(Ti_{1.1}V_1Mn_1Fe_1Mo_1)O_{11.2}$ metal oxide coated ceramic corrugated plate catalyst was obtained.

Figure 1:
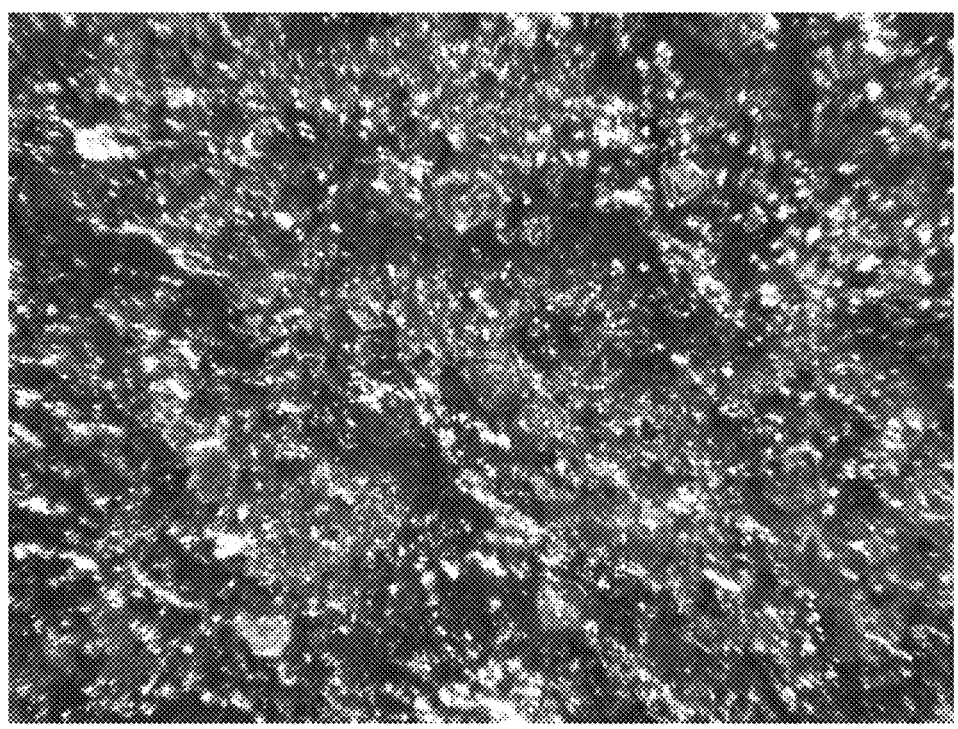
FIG. 1: a 100× micrograph of a $(Ti_{11}V_1Mn_1Fe_1Mo_1)O_{11.2}$ metal oxide coated ceramic corrugated plate catalyst.
Figure 2:
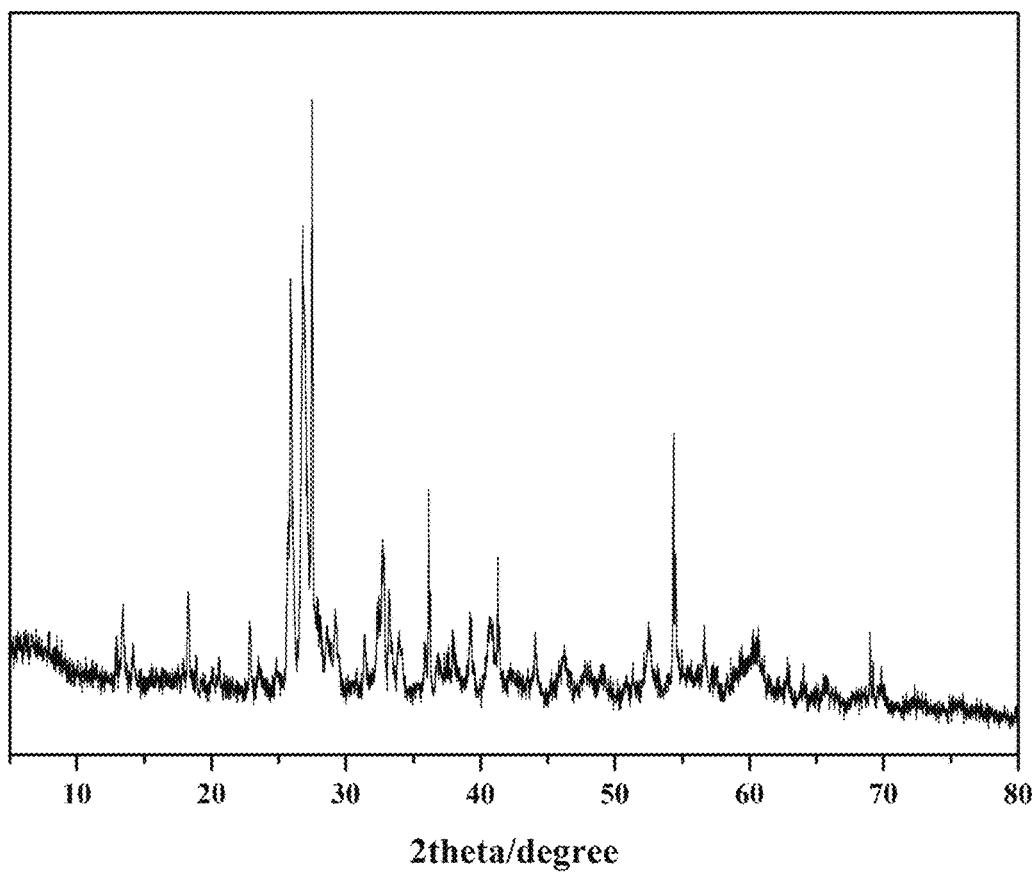
FIG. 2: an XDR characterization of the $(Ti_{1.1}V_1Mn_1Fe_1Mo_1)O_{11.2}$ metal oxide coated ceramic corrugated plate catalyst.

According to FIGS. 1 and 2, the results of the 100× micrograph and XRD diffraction test showed that the catalyst containing the above target component was prepared.

As shown in FIGS. 1 and 2, the metal oxide shown in FIG. 1 is uniform and complete in the coating area without pore channels, and does not influence the separation function of the corrugated plate; FIG. 2 is an XRD characterization of metal oxides.

Examples 2-5

According to the method of Example 1, the following catalysts (Table 1) were obtained by varying the added metal elements and the amounts thereof, the pH value of the titanium sol, the calcination temperature, and the calcination time, respectively.

TABLE 1

Catalyst Preparation Parameters for Examples 1-5

| | pH value | Calcination temperature (° C.) | Calcination time (h) | Catalyst | Catalyst Loading (%) |
|---|---|---|---|---|---|
| Example 1 | 3 | 950 | 6 | $(Ti_{1.1}V_1Mn_1Fe_1Mo_1)O_{11.2}$ | 9.8 |
| Example 2 | 3 | 700 | 6 | $(Ti_1V_1Mn_1Fe_1Mo_1)O_{11}$ | 5.0 |
| Example 3 | 3 | 1000 | 3 | $(Ti_1V_1Zr_1Fe_1Mo_1)O_{11}$ | 1.0 |
| Example 4 | 5 | 900 | 6 | $(Ti_1V_{1.2}Zr_1Cr_1Mo_1)O_{13.5}$ | 4.9 |
| Example 5 | 1 | 1000 | 3 | $(Ti_1V_1Nb_{0.8}Fe_1Mo_1)O_{11}$ | 5.0 |

Example 6

Preparation of $(Ti_{1.1}V_1Mn_1Fe_1Mo_1)O_{11.2}$ Metal Oxide Coated Ceramic Corrugated Plate Catalyst This comparative example differs from Example 1 only in that the spray drying temperature of step (2) was 200° C.

In order to better reflect the influence of the composition of the metal oxide on the catalyst, the following comparative examples were also carried out. The loading of each catalyst was as follows in Table 2.

Comparative Example 1

Preparation of $(Ti_1V_1Mn_1)O_X$ Metal Oxide Coated Ceramic Corrugated Plate Catalyst It differs from Example 1 in that in step (1), 1 mol ammonium vanadate and 1 mol manganese chloride were added to 1.1 mol titanium dioxide sol (concentration 20%, pH 3), dissolved by ultrasonic wave, and thoroughly mixed uniformly to obtain a mixed colloidal liquid.

Comparative Example 2

Preparation of $(Ti_1Fe_1Mo_1)O_Y$ Metal Oxide Coated Ceramic Corrugated Plate Catalyst It differs from Example 1 in that in step (1), 1 mol ferric trichloride and 1 mol molybdenum citrate were added to 1.1 mol of titanium dioxide sol (concentration 20%, pH 3), dissolved by ultrasonic waves, and mixed uniformly to obtain a mixed colloidal liquid.

TABLE 2

| | Catalyst Loading (%) |
|---|---|
| Example 6 | 9.8 |
| Comparative Example 1 | 9.6 |
| Comparative Example 2 | 9.8 |

Example 7

Preparation of Prenal

Figure 3:
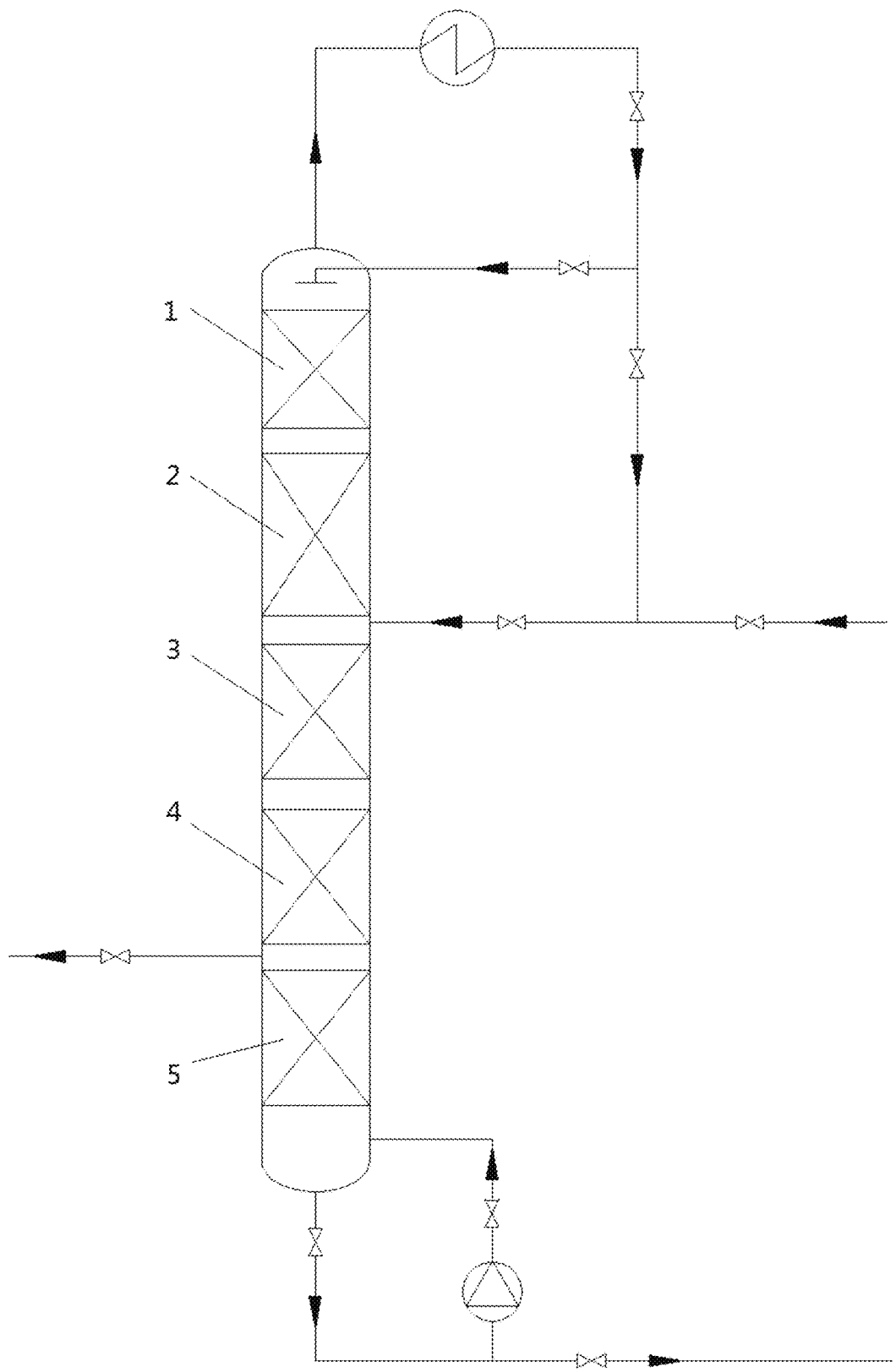
FIG. 3: a catalytic rearrangement reaction system.

Methylbutynol was continuously fed into a rectifying tower, the feeding amount was 100 Kg/h. As shown in FIG. 3, the first reaction zone 2 and the second reaction zone 3 were respectively and regularly packed with metal oxide coated ceramic corrugated plate catalyst prepared from examples 1-5 and comparative examples 1-2, of which the theoretical tray number was 5, and the first separation zone 1 was packed with common ceramic corrugated plate packings with the theoretical tray number of 10; the second separation zone 4 was packed with a common ceramic corrugated plate packing with a theoretical tray number of 25, and the third separation zone 5 was packed with a common ceramic corrugated plate packing with a theoretical tray number of 5. In the rectifying tower, controlling reaction temperature at 120-125° C., reaction pressure at 0.06 MPa and condensation temperature at top of the tower at 80° C., prenal production was started after 2 h of recycle reaction, and the results are shown in Table 3 below.

TABLE 3

| Catalyst number | Reaction time (h) | Prenal yield per hour (Kg) | Prenal purity (%) |
|---|---|---|---|
| Example 1 | 5 | 96 | 99.3 |
| Example 2 | 5 | 96 | 99.5 |

TABLE 3-continued

| Catalyst number | Reaction time (h) | Prenal yield per hour (Kg) | Prenal purity (%) |
|---|---|---|---|
| Example 3 | 5 | 95 | 99.1 |
| Example 4 | 5 | 97 | 99.4 |
| Example 5 | 5 | 95 | 99.1 |
| Example 1 | 50 | 96 | 98.7 |
| Example 1 | 100 | 96 | 97.1 |
| Example 6 | 5 | 96 | 99.1 |
| Example 6 | 24 | 96 | 58.3 |
| Comparative Example 1 | 5 | 96 | 84.3 |
| Comparative Example 2 | 5 | 96 | 78.1 |
| Comparative Example 1 | 24 | 96 | 1.3 |
| Comparative Example 2 | 24 | 96 | 0.9 |

Example 8

Preparation of Prenol

Methylbutenol was continuously fed into a rectifying tower, and the feeding amount was 100 Kg/h. The first reaction zone 2 and the second reaction zone 3 were respectively and regularly packed with metal oxide coated ceramic corrugated plate catalyst prepared from examples 1-10 and comparative examples 1-4, of which the theoretical tray number was 3 and 10, the first separation zone 1 was packed with metal oxide coated ceramic corrugated plate packing prepared from examples 1-10 and comparative examples 1-4, of which the theoretical tray number was 8, the second separation zone 4 was packed with Pall ring packing with a theoretical tray number of 28, and the third separation zone 5 was packed with Pall ring packing with a theoretical tray number of 7. Reaction temperature at 128-133° C., reaction pressure at 0.07 MPa and condensation temperature at top of the tower at 90° C., prenal production was started after 2 h of recycle reaction, and the results are shown in Table 4 below.

TABLE 4

| Catalyst number | Reaction time (h) | Prenal yield (Kg) | Prenal purity (%) |
|---|---|---|---|
| Example 1 | 5 | 95 | 99.6 |
| Example 2 | 5 | 97 | 99.2 |
| Example 3 | 5 | 96 | 99.3 |
| Example 4 | 5 | 97 | 99.1 |
| Example 5 | 5 | 96 | 98.9 |
| Example 1 | 50 | 95 | 98.9 |
| Example 1 | 100 | 95 | 98.3 |
| Example 6 | 5 | 95 | 99.3 |
| Example 6 | 24 | 95 | 60.9 |
| Comparative Example 1 | 5 | 95 | 81.2 |
| Comparative Example 2 | 5 | 95 | 79.3 |
| Comparative Example 1 | 24 | 95 | 0.73 |
| Comparative Example 2 | 24 | 95 | 1.32 |

Example 9

Following the method of Example 1, an additional 10 g dodecyl polyethylene glycol ether was added during the preparation of the mixed colloidal liquid to obtain $(Ti_{1.1}V_1Mn_1Fe_1Mo_1)O_{11.2}$ metal oxide coated ceramic corrugated plate catalyst.

Example 10

Prenal was prepared by catalytic rearrangement according to the method of Example 7 with the catalyst prepared in Example 9, and the reaction results are shown in Table 5 below.

TABLE 5

| Reaction time (h) | Prenal yield (Kg) | Prenal purity (%) |
|---|---|---|
| 5 | 96 | 99.5 |
| 10 | 96 | 99.2 |
| 20 | 96 | 98.7 |
| 50 | 96 | 98.5 |
| 100 | 96 | 98.4 |

Finally, it should be noted that the above description was only intended to illustrate the technical solution of the present disclosure and was not intended to limit the scope of the present disclosure, and that those skilled in the art will be able to make simple modifications or equivalent alterations to the technical solution of the present disclosure without departing from the spirit and scope of the technical solution of the present disclosure.

What is claimed is:

1. A metal oxide coated ceramic corrugated plate catalyst, consisting of a ceramic corrugated plate carrier and a metal oxide active layer coated on a surface of the carrier, wherein the ceramic corrugated plate carrier is made of cordierite, alumina or silicon carbide, wherein the metal oxide active layer is a metal oxide formed of active ingredients consisting of titanium, vanadium, and molybdenum and two other metal elements selected from chromium, manganese, iron, zirconium, and niobium.

2. The metal oxide coated ceramic corrugated plate catalyst according to claim 1, wherein the two other metal elements comprise manganese and iron, zirconium and iron, zirconium and chromium, or niobium and iron.

3. The metal oxide coated ceramic corrugated plate catalyst according to claim 1, wherein the loading amount of the metal oxide active layer is 0.1-10 wt % of the ceramic corrugated plate.

4. The metal oxide coated ceramic corrugated plate catalyst according to claim 1, wherein the metal oxide active layer is a metal oxide formed by Ti and four metal elements of V, Mn, Fe and Mo, wherein a molar ratio of all the metal elements in the metal oxide is 1-1.5:1-1.2:1:1:1.

5. The metal oxide coated ceramic corrugated plate catalyst according to claim 1, wherein the metal oxide active layer is a metal oxide formed by Ti and four metal elements of V, Zr, Cr and Mo, wherein a molar ratio of all the metal elements in the metal oxide is 1-1.5:1-1.2:1:1:1.

6. A method for preparing the metal oxide coated ceramic corrugated plate catalyst according to claim 1, comprising the steps of:
   (1) dissolving salts comprising vanadium, molybdenum and the two other metal elements in titanium sol to form uniform mixed colloidal liquid;
   (2) carrying out spray drying on the mixed colloidal liquid on a surface of the ceramic corrugated plate and high-temperature calcination to obtain the metal oxide coated ceramic corrugated plate catalyst.

7. The method for preparing a metal oxide coated ceramic corrugated plate catalyst according to claim 6, wherein the titanium sol is controlled to have a pH value of 1-5.

8. The method for preparing the metal oxide coated ceramic corrugated plate catalyst according to claim 6, wherein the titanium sol has a mass concentration of 10-30% and the solvent of the titanium sol is water.

9. The method for preparing the metal oxide coated ceramic corrugated plate catalyst according to claim 6, wherein the titanium sol further comprises a surfactant in an amount of 1-5 wt % of the titanium sol.

10. A method for preparing the metal oxide coated ceramic corrugated plate catalyst according to claim 2, comprising the steps of:
  (1) dissolving salts comprising vanadium, molybdenum and the two other metal elements in titanium sol to form uniform mixed colloidal liquid;
  (2) carrying out spray drying on the mixed colloidal liquid on a surface of the ceramic corrugated plate and high-temperature calcination to obtain the metal oxide coated ceramic corrugated plate catalyst.

11. A method for preparing the metal oxide coated ceramic corrugated plate catalyst according to claim 3, comprising the steps of:
  (1) dissolving salts comprising vanadium, molybdenum and the two other metal elements in titanium sol to form uniform mixed colloidal liquid;
  (2) carrying out spray drying on the mixed colloidal liquid on a surface of the ceramic corrugated plate and high-temperature calcination to obtain the metal oxide coated ceramic corrugated plate catalyst.

12. A method for continuous preparation of prenal or prenol, comprising following steps of:
  filling a reaction zone of a rectifying tower with a metal oxide coated ceramic corrugated plate catalyst, correspondingly continuously introducing methylbutynol or methylbutenol into the rectifying tower for catalytic rearrangement reaction, and continuously extracting prenal or prenol from a lateral line of the tower kettle, wherein the metal oxide coated ceramic corrugated plate catalyst consists of a ceramic corrugated plate carrier and a metal oxide active layer coated on the surface of the carrier, wherein the ceramic corrugated plate carrier is made of cordierite, alumina or silicon carbide, wherein the metal oxide active layer is a metal oxide formed with active ingredients consisting of titanium and four metal elements of V, Mn, Fe and Mo, titanium and four metal elements of V, Zr, Fe and Mo, titanium and four metal elements of V, Zr, Cr and Mo, or titanium and four metal elements of V, Nb, Fe and Mo.

13. The method for continuous preparation of prenal or prenol according to claim 12, wherein the loading amount of the metal oxide active layer is 0.1-10 wt % of the ceramic corrugated plate.

14. A method for continuous preparation of prenal or prenol, comprising following steps of:
  filling a reaction zone of a rectifying tower with the metal oxide coated ceramic corrugated plate catalyst according to claim 4, correspondingly continuously introducing methylbutynol or methylbutenol into the rectifying tower for catalytic rearrangement reaction, and continuously extracting prenal or prenol from a lateral line of the tower kettle.

15. A method for continuous preparation of prenal or prenol, comprising following steps of:
  filling a reaction zone of a rectifying tower with the metal oxide coated ceramic corrugated plate catalyst according to claim 5, correspondingly continuously introducing methylbutynol or methylbutenol into the rectifying tower for catalytic rearrangement reaction, and continuously extracting prenal or prenol from a lateral line of the tower kettle.

* * * * *